United States Patent [19]

Tansamrit et al.

[11] Patent Number: 4,975,173
[45] Date of Patent: Dec. 4, 1990

[54] ELECTROPHORESIS PLATE AND METHOD OF MAKING SAME

[75] Inventors: Subphong Tansamrit, Beaumont; Philip A. Guadagno, Vidor, both of Tex.

[73] Assignee: Helena Laboratories Corporation, Beaumont, Tex.

[21] Appl. No.: 313,764

[22] Filed: Feb. 22, 1989

[51] Int. Cl.$^5$ ............... G01N 27/26; B01D 57/02
[52] U.S. Cl. ............... 204/299 R; 204/183.8
[58] Field of Search ........... 204/299 R, 182.8, 182.9, 204/182.7, 180.1

[56] References Cited

U.S. PATENT DOCUMENTS

| | | | |
|---|---|---|---|
| 3,432,414 | 3/1969 | Rand | 204/299 R |
| 3,432,424 | 3/1969 | Zec | 204/182.7 |
| 3,479,265 | 11/1969 | Elevitch | 204/182.8 |
| 3,674,678 | 7/1972 | Post, Jr. et al. | 204/299 R |
| 3,751,357 | 8/1973 | Rains | 204/182.8 |
| 3,764,513 | 10/1973 | Saravis | 204/182.8 X |
| 4,874,491 | 10/1989 | Stålberg | 204/182.8 |
| 4,892,639 | 1/1990 | Sarrine et al. | 204/299 R |

Primary Examiner—John F. Niebling
Assistant Examiner—John S. Starsiak, Jr.
Attorney, Agent, or Firm—Spencer & Frank

[57] ABSTRACT

An electrophoresis plate of the type including a base layer of an electrophoretic medium containing some buffer material and a method of making such an electrophoresis plate. On the base layer of the plate there are formed buffer blocks made up of an electrophoretic medium having a lower electroendosmotic potential than that of the base layer. The buffer blocks contain buffer material for functioning as a self-contained reservoir during electrophoresis. The method of the present invention includes continuous casting of the buffer blocks and also includes casting the buffer blocks as a sequence of discrete layers.

33 Claims, 4 Drawing Sheets

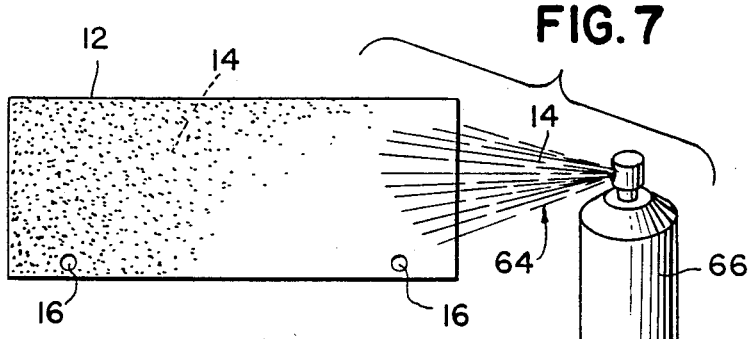
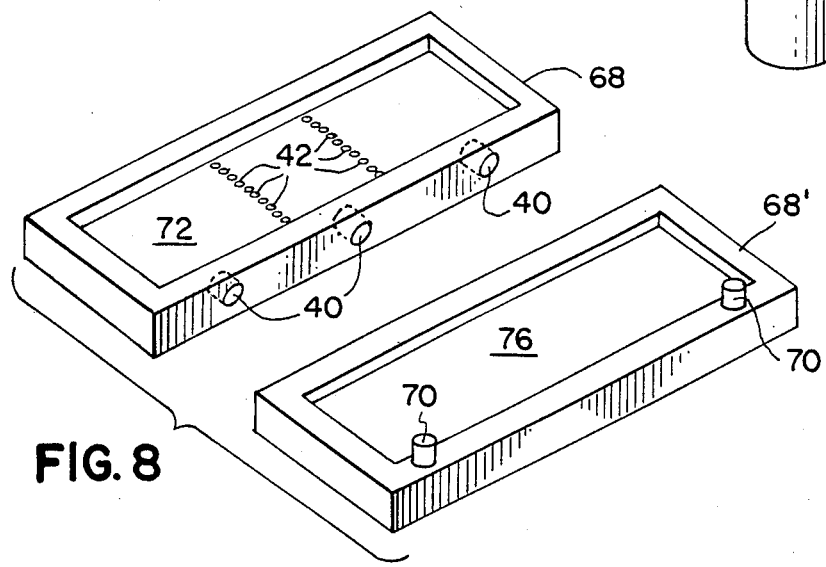
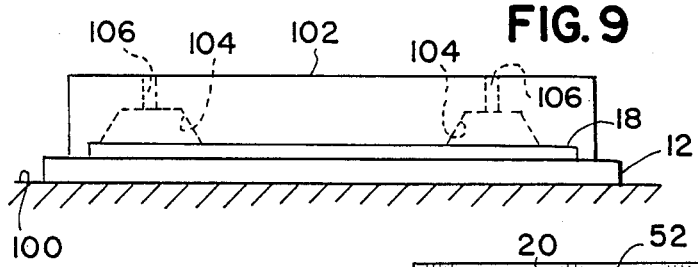
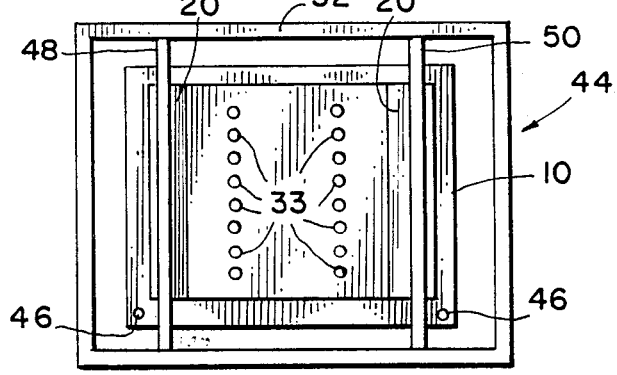

ELECTROPHORESIS PLATE AND METHOD OF MAKING SAME

CROSS-REFERENCE TO RELATED APPLICATION

The present application is an improvement of the invention of an Electrophoresis Plate and Method of Making Same as described in the copending application of Sarrine, et al., filed July 17th, 1987, as Application Ser. No. 07/074,584, now U.S. Pat. No. 4,892,634 and assigned to the assignee of the present invention. The disclosure of the aforementioned application is incorporated by reference.

BACKGROUND OF THE INVENTION

The present invention relates to improvements in electrophoresis plates and methods of making such plates. By way of background, electrophoresis is a well-established method for separation of biochemicals, and is useful in the analysis of proteins found in complex physiological fluids and tissue. Typically, electrophoresis is carried out in a separation medium, for example a polymer gel such as agarose or polyacrylamide. Of course, cellulose acetate is also used as a separation medium.

In the formation of the electrophoresis plates, the electrophoretic or polymer gel is cast in molds and secured to an inert substrate. In the electrophoresis process, numerous samples are typically placed on the electrophoretic medium, i.e., the polymer gel. To effect the electrophoretic separation, an electric field is established with respect to the gel containing the samples. One common practice has been to immerse the opposite ends of the electrophoresis plate into reservoirs of electrically conductive buffers which are provided to maintain the pH of the electrophoresis process. The buffers are connected to electrodes, the electrodes are connected respectively to the positive and negative terminals of a power supply, and this establishes a voltage gradient across the electrophoresis plate. In response to the voltage gradient, the molecules in the samples migrate across the electrophoretic medium in proportion to various factors such as the charge and size of the protein molecules. All of the foregoing is, of course, well-known.

Rather than immersing the ends of the electrophoresis plate into the buffers an alternate technique has been developed known as "wicking" in which an absorbent wick or piece of paper is used to connect each buffer to its respective end of the electrophoresis plate. This technique is also conventional.

When the electrophoretic separation has been completed, it is typical to place the electrophoresed sample under ultraviolet light. Normally, the gel (such as agarose gel) is essentially colorless, the inert plastic (typically polyester) or glass substrate is transparent, and a piece of dark or black paper is placed under the substrate such that the fluorescence of the sample would be visible. Thus optical contrast was provided by the dark paper such that the results of the electrophoresis could be more easily determined and interpreted.

The present invention provides numerous benefits with respect to the electrophoresis plate and the method of making and using the same, as will be hereinafter described.

SUMMARY OF THE INVENTION

The present invention provides an electrophoresis plate of the type including a base layer of an electrophoretic medium containing some buffer material and a method of making such an electrophoresis plate. The base layer is associated with a substrate which is chemically and electrically inert. On the base layer of the plate there are formed buffer blocks comprising an electrophoretic medium or electrophoretic mediums which have a lower electroendosmotic potential than that of the base layer. The buffer blocks are gels containing buffer material plus water (if the buffer material contains water) for functioning as a self-contained buffer reservoir.

BRIEF DESCRIPTION OF THE DRAWINGS

The various features, benefits and advantages of the present invention will become more apparent upon reading the following detailed description of the invention in conjunction with the drawings. In the drawings:

FIG. 7 is a diagrammatic view of priming the inert substrate as a first step in the method of making the electrophoresis plate of the present invention.

FIG. 8 is a diagrammatic illustration of a mold which may be used to cast or coat the base layer onto the substrate according to the present invention.

FIG. 9 is an end view of the use of a capping mold to add the buffer blocks to the electrophoresis plate according to the present invention.

FIG. 10 is a plan view of a typical electrophoretic chamber illustrating the electrodes properly aligned relative to the buffer blocks through the use of alignment holes.

DETAILED DESCRIPTION OF THE INVENTION

Figure 1:
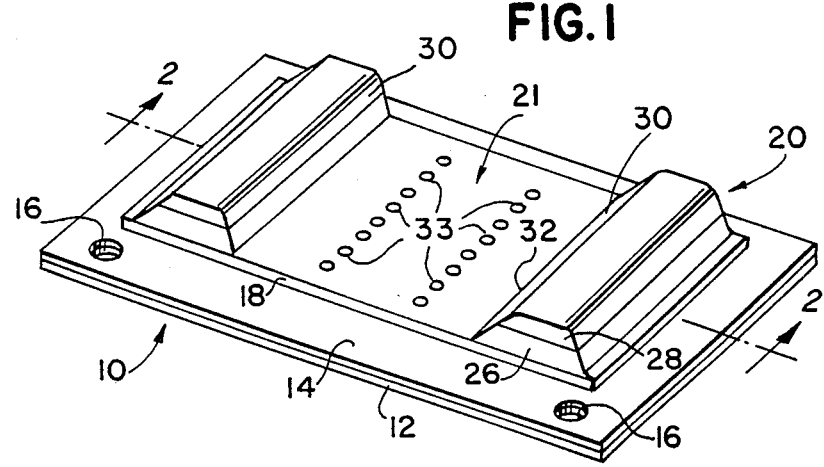
FIG. 1 is a perspective view of an electrophoresis plate made in accordance with the principles of the present invention.

Referring first to the electrophoresis plate 10 of one embodiment of the invention as illustrated in FIG. 1, the plate includes a substrate 12 of a substance which is both electrically and chemically inert. The substrate may be selected from of one of many materials that are conventionally used as supports for electrophoretic gel media and have the desired degree of rigidity to support and protect the gel from damage during handling and shipment. Film materials that are suitable for this purpose include polystyrene, polyethylene and glass, as well as polyesters. A preferred substrate is a polyester film sold by E.I. duPont DeNemours and Company under the trademark Mylar and, if the electrophoresed sampled is to be subjected to ultraviolet light, it is desirable to use a dark or black Mylar. An alternative substrate which is equally satisfactory is a thermoplastic polycarbonate film sold by General Electric under the trademark Lexan. Again, the film should be dark or black if the electrophoresed sample is to be evaluated under ultraviolet light.

The following explanation will be given assuming that agarose gel is to be used as the electrophoretic medium. However, it should be understood that according to the principles of the present invention, other electrophoretic media may be used. This includes, without limitation, the use of polyacrylamide whether cross-linked or not, regardless of whether a catalyst is present.

Figure 2:
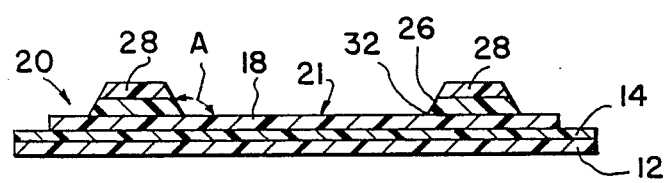
FIG. 2 is a cross-sectional view of the electrophoresis plate of FIG. 1 taken in the direction of arrows 2—2.

Referring to FIGS. 1 and 2, the substrate 12 is typically prepared by first applying a primer or gel bonding layer 14 to the substrate. The primer layer or film 14 would be a thin coating of agarose gel. It is preferable to provide one or more alignment holes 16 through the plate 10 such that the plate may be aligned relative to the electrodes when the voltage gradient is to be applied to the samples. The alignment holes may be provided either before or after the substrate is coated with the primer layer 14. If the alignment holes are provided after the primer layer is applied, then since the primer layer may cover the entire substrate, the alignment holes may extend through the primer layer as well as through the substrate. The alignment holes are illustrated as extending through the plate and are illustrated as being adjacent to one edge of the plate 10. The number of alignment holes and their precise location may, of course, be varied within the spirit of the present invention.

Positioned above the primer layer 14 is the electrophoretic gel generally illustrated as a large, thin rectangular layer 18. The precise shape of the gel layer is not limited to rectangular or square and hence the reference to a rectangular layer is for illustrative purposes only. Gel layer 18 may be referred to as the base layer.

At each of the opposite ends of the base layer 18 and in contact with the base layer, a buffer block 20 is provided. In the preferred embodiment of the present invention, the buffer blocks preferably extend at least about 0.100 inches above the top surface 21 of the base layer 18. These buffer blocks 20 provide the buffer reservoir for electrophoresis. The buffer blocks alone or in combination with the base layer are laminates, i.e., there are a plurality of layers.

During the electrophoresis process, certain phenomenon occur which may interfere with or adversely influence the electrophoresis. For example, during the heat build-up associated with the voltage gradient, water which is present in the gel tends to become more mobile and will tend to flow. If there is excessive water flow, there is a blurring and broadening of the electrophoresis zones thus interfering with the analysis of the electrophoresed sample. Another problem which occurs as a result of heat build-up is the actual collapse of the buffer blocks which is referred to as gel melt. These are problems with typical commercial agarose gel media. Gel melt may even occur when a thin layer of agarose gel is placed on a substrate and electrophoretic separation is performed using the aforementioned wicking technique without the use of buffer blocks.

It is known that commercial agarose gels have different degrees of impurities, such as sulfates and/or pyruvates, which may be correlated to the degree or extent of water movement in response to a voltage differential and heat. The tendency of the water to migrate or move in response to fixed, ionically charged molecules in the gel when a voltage differential is applied, is referred to as electroendosmosis.

In electrophoresis using a thin gel layer with either wicks or immersing the ends of the gel layer into liquid buffers, it is well known to obtain a degree of control on the extent of electroendosmosis (EEO) by using more or less pure forms of agarose gel. One such more pure gel is sold under the trademark Isogel. While it would be desirable to use a more pure product, which has a low EEO, when buffer blocks are to be cast or molded onto a substrate the large volume of gel makes the cost of the entire plate too expensive since the cost of the media increases with increases in purity.

The present invention has overcome the problems associated with high EEO gels while maintaining all the advantages of a solid gel buffer block system, and while avoiding the high cost associated with using only low EEO gels. According to the principles of the present invention, the buffer blocks are formed as a composite or laminate, where low EEO gel is used in the plate in the area of expected heat build-up, such as in the region of the electrodes where the problems of water movement are most acute. A lower EEO medium is also more resistant to "gel melt" due to heat build up at an electrode than a higher EEO medium. That is to say, even if there is gel melt with a low EEO medium, the water in the gel does not flow as readily as the water in a high EEO gel. However, according to the principles of the present invention, while a low EEO gel is used in the region of expected heat build-up, a higher EEO gel is used in the remainder of the buffer blocks and the remainder of the plate. This aids in controlling the cost of the electrophoresis plate. The lower EEO medium may be a more pure form of the higher EEO medium used elsewhere in the plate or an entirely different type of electrophoretic medium.

In the embodiment shown in FIGS. 1 and 2, each buffer block 20 includes a lower layer 26, which contacts the base layer 18, and an upper layer 28 which contacts the lower layer 26. Thus the buffer block as illustrated in FIGS. 1 and 2 may be considered a gel block formed as a laminate. The width of the layers are reduced as the height of the buffer block increases above the substrate. In the embodiment of FIGS. 1 and 2, the layer 28 would have the lowest EEO and the layer 18 would have the highest EEO, and the layer 26 could have either an intermediate EEO or be the same material and purity (and thus the same EEO) as the layer 18. Hence, depending upon the gels selected, the buffer region or buffer block may be considered as two or three layers.

Figure 3:
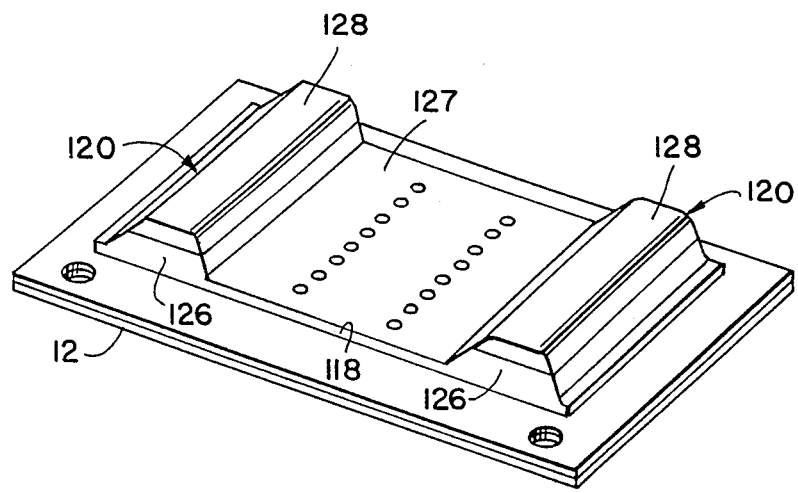
FIG. 3 is a perspective view of another electrophoresis plate made in accordance with the principles of the present invention.

In an alternative embodiment shown in FIG. 3, an electrophoresis plate including a gel base layer 118 and buffer blocks 120 is illustrated on one side of the substrate 12. The gel base layer 118 has end portions 126 which are thicker than the intermediate portion 127 of the base layer 118. Thus, the base layer end portions 126 extend above the top of the intermediate portion 127 of the base layer 118. The gel used for the base layer 118, including the raised end portions 126, have a first or higher EEO. In this embodiment, an upper layer 128 of lower EEO medium is positioned on top of the raised portion 126. Thus each of the buffer blocks 120 in this embodiment are composites or laminates of two layers 126, 128 of electrophoretic media. When an electrode, such as the type illustrated in FIG. 10 contacts the top of the buffer block 120, the electrode is in contact with the lower EEO gel layer 128. However, by providing a buffer block 120 where a larger portion 126 of the block is of the same material as the gel layer 118, less of the expensive, low EEO material is utilized than if the entire gel buffer block was formed of a low EEO gel.

Figure 4:
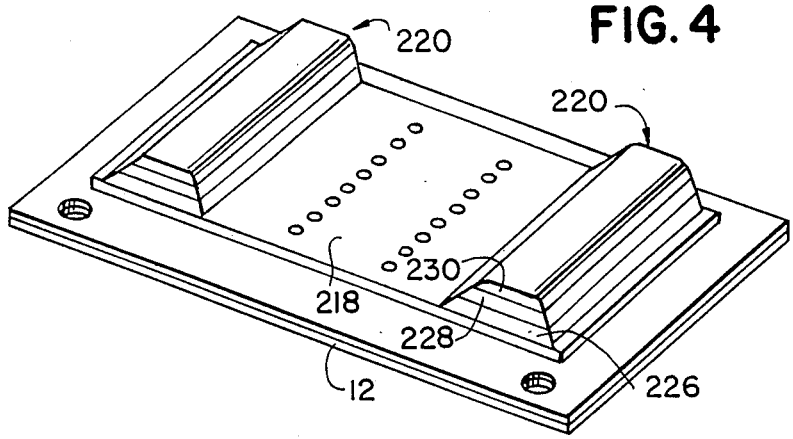
FIG. 4 is a perspective view of yet another electrophoresis plate made in accordance with the principles of the present invention.

Referring next to the embodiment of FIG. 4, an electrophoresis plate includes a substrate 12, a base gel layer 218, and buffer blocks 220 at opposite ends of the base gel layer. The blocks 220 are illustrated as having three gel laminates or layers: a lower layer 226, an intermediate layer 228, and an upper layer 230. In this embodiment, the EEO of each of the gel layers will be lower than the immediately preceding layer as the layers are more distant from the substrate. Thus, layer 230 would have the lowest EEO, layer 228 the next lowest EEO, layer 226 the next lowest EEO, and layer 218 the highest EEO. This may also be explained as a buffer block where the EEO decreases (or at least does not increase) as the distance from the substrate increases. Again, the width of the buffer blocks also decreases as the height above the substrate increases.

In each of the embodiments already described, each interface between adjacent gel layers within the gel buffer block has been illustrated as generally parallel to the flat, inert substrate 12.

Figure 5:
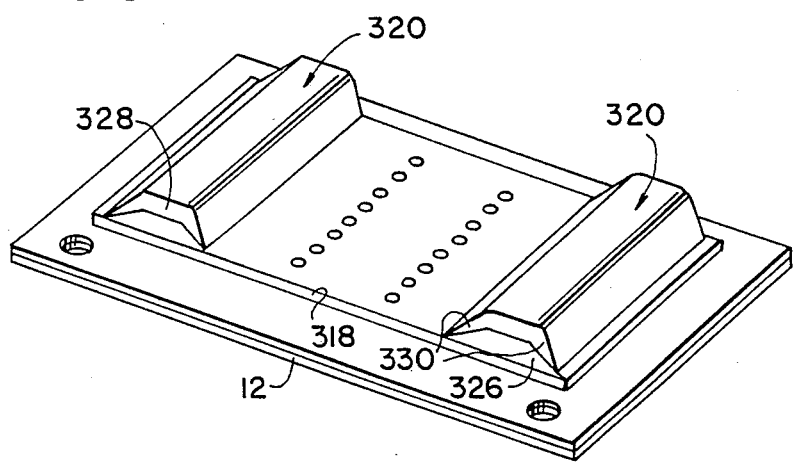
FIG. 5 is a perspective view of another electrophoresis plate made in accordance with the principles of the present invention.

Referring next to the embodiment illustrated in FIG. 5, an electrophoresis plate includes a substrate 12 upon which is positioned an electrophoresis base gel layer 318. At each end of the layer 318 are buffer blocks 320. According to the principles of the invention as illustrated in FIG. 5, each gel block 320 includes a lower layer 326 and an upper layer 328, with the upper layer formed of a gel having a lower EEO than the EEO of the lower layer 326. However, rather than an interface between the upper and lower layers of the gel block which is parallel to the substrate 12 (as viewed in cross-section) the upper layer 328 includes opposed beveled or chamfered portions 330 which extend downward on opposite sides of the buffer block 320 toward the substrate 318. The use of a chamfered or beveled upper gel layer increases the amount of low EEO medium in the region immediately surrounding where an electrode will be in contact with the buffer block 320.

It is within the spirit and scope of the present invention that the configuration of FIG. 5 with a chamfered or beveled interface between the gel layers may be utilized in any of the embodiments of the present invention.

Figure 6:
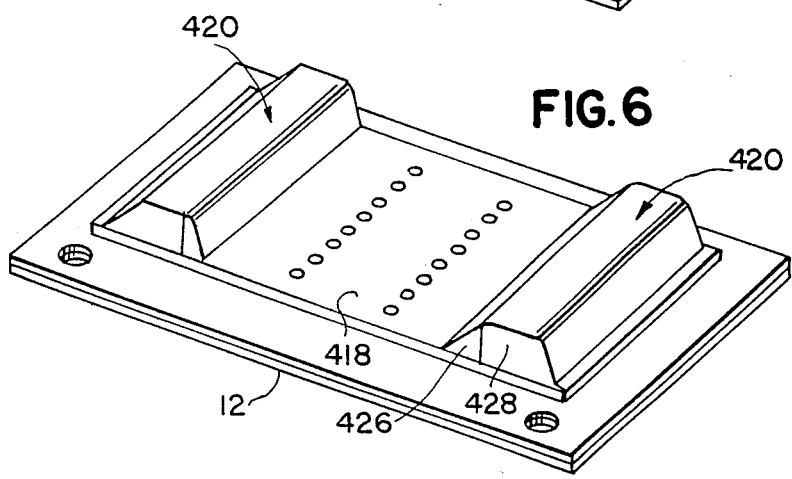
FIG. 6 is a perspective view of still another electrophoresis plate made in accordance with the principles of the present invention.

Referring next to FIG. 6 the electrophoresis plate includes an inert substrate 12 (which, of course, is a common feature of all the electrophoresis plates) having a gel base layer 418 thereon. Positioned at each end of the gel layer 418 is a gel buffer block 420. While the prior embodiments illustrate and describe buffer block layers which have constant or decreasing EEO as the distance from the substrate increases, the embodiment of FIG. 6 is of slightly different configuration while still functioning to reduce, if not eliminate, undesirable water flow. In the embodiment of FIG. 6, each buffer block 420 includes an intermediate component 426 of a first EEO medium, and an end component 428 laterally outwardly of the intermediate component 426. The end or outward components or layers 428 of the buffer blocks are of a gel medium which has a lower EEO than the EEO of the gel medium used for the intermediate component or layer 426. By way of clarification, and solely for the purposes of example and not limitation, in the embodiment of FIG. 6, the intermediate component 426 of the buffer block is generally triangular in cross-section and the end components 428 are generally trapezoidal in cross-section. The configuration of FIG. 6 is based upon the principle that if heat build-up occurs at a location other than (or in addition to) the contact between the gel and the electrodes, then low EEO gel may be positioned in the areas of heat build-up to compensate for any heat build-up or gel melt.

In each of the embodiments heretofore illustrated, the buffer blocks are generally trapezoidal in cross-section when viewed from the longer side of the plate. Such shape is for illustrative purposes only. As illustrated in greater detail in FIGS. 1 and 2, each buffer block is generally trapezoidal with an upper short surface and a lower long surface parallel to each other, and with sloping or tapered sides therebetween. The upper and lower surfaces are parallel to the substrate 12. The tapered or sloping sides 30 of the buffer blocks which face each other are preferably at an angle of at least 135 degrees, relative to the surface of the substrate, identified as angle A in FIG. 2, to prevent burning at the weakest edge 32. Edge 32 is defined as the interface between the electrophoresis surface of the gel layer 18, where the samples are electrophoresed and the sloping face or side 30 of the buffer block 20. An additional advantage of the tapered buffer block configuration is to aid in their removal from a mold where they are formed or cast, as will be described.

According to the principles of the present invention, the primer layer of the electrophoresis plate may be several microns thick, the electrophoretic base layer 18 may be 0.18 inches thick, and the buffer blocks should be between about 0.100 to about 0.150 inches thick, in addition to the thickness of the gel base layer 18. Of course these dimensions are illustrative as to the relative size of the layers according to the preferred embodiment of the invention, and should not be interpreted as a limitation of the present invention.

The gel base layer 18 may also be provided with a series of sample apertures 33. In the embodiment shown in FIG. 1, two series or rows of apertures are provided. The sample apertures are aligned perpendicular to the elongated axis of the plate 10 and parallel to the elongated axes of the buffer blocks 20.

The substrate is typically rectangular in configuration and may be corona charged to accept a liquid gel. It should be understood that in the first instance the substrate is chemically and electrically inert, and thus the electrophoretic layer would not form a suitable coating or layer, but would rather form a series of discrete droplets on the surface of the substrate. Thus, the use of a corona charge on the substrate to allow adherence of the electrophoretic layer and allow the layer to gel is a common technique, referred to as priming the substrate.

Thus referring to FIG. 7, a first step in one method of making the electrophoresis plate of the present invention is the primer layer of gel 14 being applied via a spray 64 from a container 66. The primer layer may be the same electrophoretic medium as the subsequent electrophoretic gel layer although more dilute. It should be understood that this is diagrammatic only and, in FIG. 7, the primer 14 is illustrated as covering the substrate. It is common to prime an electrophoresis plate, such as by a spray technique, or alternatively, by dipping the substrate in a dilute solution of gel and thereafter removing the excess solution via a squeegee or the like. The primer layer is allowed to cure or gel. Then, alignment holes 16 may be provided in the substrate 12. (Alternatively, alignment holes may be provided prior to priming.) If "built-in" electrodes are desired they may be placed on the substrate prior to the application of the primer 14.

FIG. 8 illustrates diagrammatically the apparatus for the second step in the preferred method of making the electrophoresis plate of the present invention. This second step may be considered the formation of the base gel layer on the substrate in a closed mold. FIG. 8 illustrates first and second press mold halves 68 and 68', respectively, each having a generally rectangular configuration. A pair of pins 70 extends upwardly from the top surface of the second mold half 68', to be received within the alignment holes 16 in the plate. The first mold half 68 has a generally rectangular mold cavity 72. The second mold half 68' has a generally rectangular mold cavity 76 which is aligned with the mold cavity 72 when the mold halves are closed. With a primed substrate placed on top of the second mold half 68', the other mold half 68 is brought down on top of the substrate, and the pins 70 extend through the alignment holes 16 Then the agarose gel is introduced into the mold. For the purpose of introducing the agarose gel into the mold, a plurality of inlets 40 are provided in the wall of the first mold half 68. Three such inlets are illustrated in FIG. 8. Shallow pins 42 in the mold cavity 72 provide apertures 33 in the electrophoresis layer 18 during molding which apertures assist in locating the samples during electrophoresis.

After the base gel layer 18 partially cures, the mold halves are opened and the substrate 12 is placed on a metal platen generally designated 100 in FIG. 9. A capping mold 102 rs placed over the base gel layer 18. The capping mold 102 includes cavities 104 for the buffer blocks and inlets 106 connected to each cavity 104. Then the lower EEO gel is introduced through inlets 106 into the cavities 104. In forming the electrophoresis plate of FIG. 4, for example, gels of decreasing EEO are sequentially introduced through inlets 106, to form layers 226, 228 and 230, respectively. Each layer may be allowed to partially set before the next layer is introduced. Thus the buffer blocks may be considered as end caps on the electrophoresis plate. Capping mold 102 is removed after the buffer block is sufficiently cured to maintain its configuration.

The present invention further contemplates combining mold half 68 with the capping mold 102 such that the substrate with the base gel layer thereon need not be removed from mold half 68'.

In use of the electrophoresis plate, the samples are placed in the apertures 33, and the assembly is placed in an electrophoretic chamber illustrated somewhat diagrammatically in FIG. 10. The electrophoretic chamber 44 includes alignment pins 46 extending upwardly from the base of the chamber with the alignment pins extending through the apertures or alignment holes 16 in the electrophoresis plate 10. With the alignment pins properly positioned within the alignment holes, the buffer blocks 20 will be properly aligned under the electrodes 48, 50 within the electrophoretic chamber 44. The electrodes are shown as attached to one wall 52 of the chamber 44. During electrophoresis, buffer gel moves from one block, across the plate, toward the other block. By having the proper alignment of the electrodes relative to the buffer blocks, the potential gradient will remain constant across the full width of the electrophoresis plate and sufficient buffer will be provided across the full width of the plate such that the results of the electrophoresis will have sufficient reliability. By utilizing the laminated or composite buffer blocks according to the principles of the present invention, there is a substantial reduction, if not elimination, in the movement of water from the buffer blocks in the region of the electrodes, thus increasing the reliability of the results of the electrophoresis.

Figure 11:
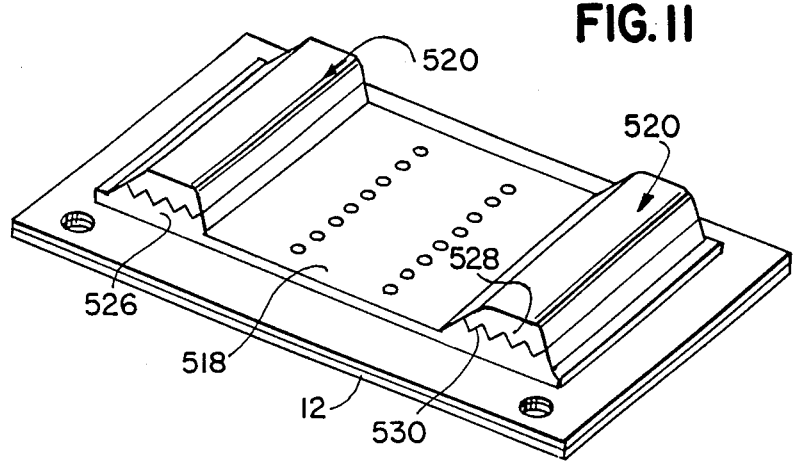
FIG. 11 is a perspective view of another electrophoresis plate made in accordance with the principles of the present invention.

Having thus described several embodiments of the electrophoresis plate of the present invention and a method of manufacturing the plate according to the present invention, reference should now be had to FIG. 11 where another embodiment of the electrophoresis plate is illustrated. The electrophoresis plate of the invention as shown in FIG. 11 includes a substrate 12 having a first thin layer of gel 518 thereon, and buffer blocks 520 at opposite ends of the gel layer 518. Each buffer block 520 is formed of lower and upper layers 526, 528, respectively, having a sawtooth or corrugated interface 530 therebetween. This form of interface will enhance the cohesion between the layers within the buffer block. Consistent with the explanation of the other embodiments of the electrophoresis plate, upper gel layer 528 has a lower EEO than the EEO of the lower gel layer 526.

Figure 12:
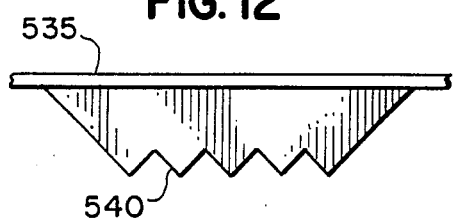
FIG. 12 is an end view of a portion of a mold member to be used in making the buffer blocks of the embodiment of FIG. 11.

To form the buffer blocks 520 of FIG. 11, reference should be had to FIG. 12 which illustrates, in end view, a mold member for forming the corrugated interface between the gel layers within the buffer block. After the gel layer 526 with the higher EEO has been cast, a mold plate 535 having a sawtooth or corrugated surface 540 is placed on the gel layer 526. Gel layer 526 is allowed to partially cure or set, then the mold plate 535 removed, and the gel layer 528 is cast in place. Of course the technique as described requires opening the capping mold to insert (and later remove) the mold plate 535.

Figure 13:
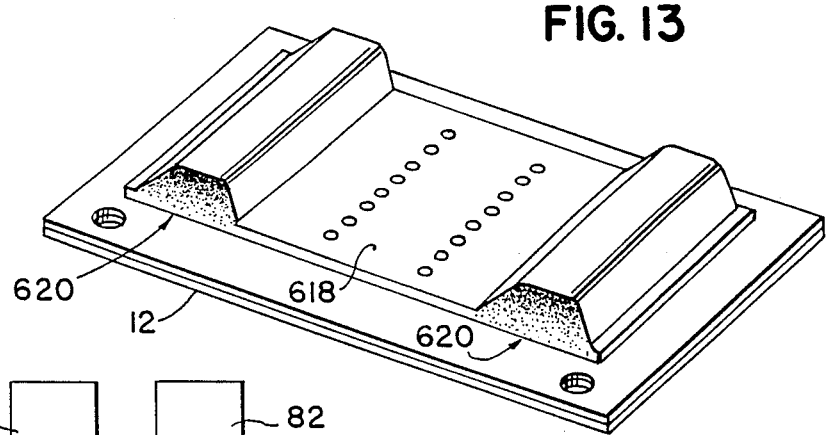
FIG. 13 is a perspective view of another electrophoresis plate made in accordance with the principles of the present invention.

The various embodiments of the present electrophoresis plate have been described and illustrated where the buffer blocks are laminate or composite discrete layers. The principles of the present invention are achieved by varying the EEO of the gel block as a function of distance from the electrode and distance from the substrate (or gel layer surface where the samples are actually deposited for electrophoresis. These principles may be achieved where the gel layer is actually a continuum of changing EEO. That is to say, the buffer block may be formed as a continuous casting, rather than as discrete castings, where the EEO of the gel is changed during the continuous casting process. An electrophoretic plate according to these teachings is illustrated in FIG. 13 where the electrophoresis layer 618 is formed on a substrate 12 and the buffer blocks 620 are formed on opposite ends of the electrophoresis base layer. The buffer blocks 620 are shaded to indicate progressively changing EEO. It is within the spirit and scope of the embodiment of FIG. 13 that the layer 618 may be cast, allowed to partially cure, and then the buffer blocks 620 cast, or alternatively a complete continuous casting of buffer blocks and layer.

Figure 14:
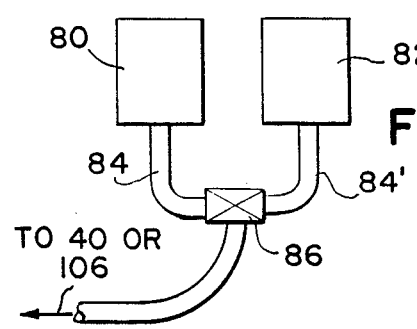
FIG. 14 illustrates diagrammatically a method for making the electrophoresis plate of FIG. 12.

An apparatus for forming the gel as a continuous casting will now be described with reference to FIG. 14. Two supply tanks 80 and 82 are provided, one supply tank containing a gel medium having a low EEO and the other supply tank containing a gel medium having a high EEO. The output of each supply tank is connected by conduits 84, 84', respectively, to a proportional mixing valve 86. Proportional mixing valve 86 controls the relative amount of each of the gel media which flow through the valve and exit the valve via conduit 88.

If a capping mold is utilized for the continuous casting, then the conduit 88 is connected to the inlets 106 If the base layer 618 and blocks 620 are formed as a continuous casting then the capping mold 102 and mold half 68 may be combined. Alternatively, continuous casting as described in the aforementioned copending application may be employed.

If capping mold 102 is utilized during the molding of the electrophoresis blocks 620, as the gel media starts to fill the enlarged mold cavity portions 104, the proportional mixing valve will be adjusted so that generally only higher EEO gel will initially pass through the mixing valve. As the enlarged mold cavity portions start to fill, the proportions of low EEO and high EEO gel media are changed, to gradually reduce the amount of high EEO gel and gradually increase the amount of low EEO gel, until the gel which is to form the top of blocks 620 will be generally all low EEO gel media. In this fashion, there is a continuum or gradually changing degree of EEO from the substrate to the top of the buffer block. Thus, it may be understood that the present invention contemplates both a gradually changing EEO (a continuum) as well as discrete layers of different EEO, within the end caps (buffer blocks).

The foregoing is a complete description of preferred embodiments of the invention. Various changes may be made without departing from the spirit and scope of the present invention. The invention, therefore, should be limited only as set forth in the claims.

What is claimed is:

1. In an electrophoresis plate of the type including a substrate which is chemically and electrically inert, relative to electrophoretic separation, and a base layer of an electrophoretic medium, the electrophoretic medium including at least some buffer, and
   buffer blocks disposed on said base layer, each of said buffer blocks including an electrophoretic medium and buffer for functioning as a self-contained buffer reservoir for electrophoresis, the improvement comprising:
   the electrophoretic medium in said buffer blocks having an electroendosmotic potential which generally decreases as the thickness of the buffer blocks increase when measured in a direction away from the substrate.

2. The invention as described in claim 1 wherein said electroendosmotic potential decreases in discrete intervals in said direction away from the substrate.

3. In an electrophoresis plate of the type including a substrate which is chemically and electrically inert, relative to electrophoretic separation, and a base layer of an electrophoretic medium, the electrophoretic medium including at least some buffer, the improvement comprising:
   buffer blocks disposed on said base layer, each of said buffer blocks including an electrophoretic medium having an electroendosmotic potential lower than the electroendosmotic potential of said base layer.

4. The invention as defined in claim 3 wherein said buffer blocks comprise a plurality of sequentially disposed laminated layers of electrophoretic media, at least one of said laminated layers having a lower electroendosmotic potential than the electroendosmotic potential of said base layer.

5. The invention as defined in claim 4 wherein the layer disposed farthest from said base layer has a lower electroendosmotic potential than the electroendosmotic potential of said base layer.

6. The invention as defined in claim 5 wherein said buffer block includes an intermediate laminate layer having an electroendosmotic potential intermediate the electroendosmotic potentials of said base layer and said layer disposed farthest from said base layer.

7. The invention as defined in claim 4 wherein each of said buffer blocks comprises two laminated layers.

8. The invention as defined in claim 4 wherein each of said buffer blocks comprises at least three laminated layers.

9. The invention as defined in claim 4 wherein the laminated layer farthest from said base layer includes polyacrylamide.

10. The invention as defined in claim 3 wherein each of said buffer blocks includes spaced apart opposing sides, the spaced apart opposing sides being tapered such that the distance between the buffer blocks decreases at said base layer 11. The invention as defined in claim 10 wherein the angle of taper of said spaced apart, opposing sides is at least 135 degrees relative to the plane of said substrate.

12. The invention as defined in claim 3 wherein said buffer block is at least about 0.100 inches thick when measured above the surface of said base layer.

13. The invention as defined in claim 3 wherein said substrate is black in color for providing color contrast of a sample electrophoresed thereon.

14. The invention as defined in claim 3 wherein adjoining laminated layers include mating corrugations therebetween 15. The invention as defined in claim 3 wherein said substrate provides color contrast of a sample electrophoresed thereon relative to ultraviolet fluorescence.

16. The invention as defined in claim 3 wherein the electrophoresis plate includes a primer coat of electrophoretic medium intermediate the substrate and the base layer.

17. The invention as defined in claim 3 wherein said base layer includes agarose.

18. The invention as defined in claim 3 wherein each of said buffer blocks extends substantially the full width of the base layer.

19. The invention as defined in claim 4 wherein one of said laminated layers includes a beveled portion which extends toward said base layer.

20. The invention as defined in claim 3 wherein each of said buffer blocks includes a portion of said base layer raised relative the rest of said base layer and a body portion adjacent to the raised portion of said base layer, said body portion being comprised of a electrophoretic medium having a lower electroendosmotic potential than the electroendosmotic potential of said base layer.

21. The invention as defined in claim 3, wherein each of said buffer blocks comprises a continuum of layers of electrophoretic media, sequentially disposed relative to said base layer, each of said layers including an electrophoretic medium having no greater an electroendosmotic potential than the electroendosmotic potential of next adjacent layer in a direction toward said base layer.

22. The invention as defined in claim 21 wherein said buffer block and said base layer comprise a unitary structure.

23. The invention as defined in claim 22 wherein the portions of said base layer beneath said buffer blocks are raised relative to the rest of said base layer.

24. The invention as defined in claim 3 wherein the side of the buffer block directly adjacent the base layer and the portion of the base layer directly adjacent the aforementioned side of the buffer block each have a plurality of mating ridges.

25. In a method of forming an electrophoresis plate of the type including a substrate which is chemically and electrically inert, relative to electrophoretic separation, and forming a base layer of electrophoretic medium thereon, the electrophoretic medium including at least some buffer, the improvement comprising:

forming buffer blocks on said base layer in adherence thereto, said buffer blocks comprising a electrophoretic medium having a lower electroendosmotic potential than the electroendosmotic potential of said base layer.

26. The method of claim 25 wherein said buffer block forming step further comprises sequentially disposing and adhering a plurality of laminated electrophoretic media layers to form a laminated buffer block.

27. The method of claim 26 wherein the buffer block forming step further comprises successively adding the medium for each layer of the block into a cavity of a mold, each said layer being allowed to partially set before adding the succeeding layer, said cavity being generally in the shape of said block.

28. The method of claim 27 further comprising the step of molding said base layer together with said buffer blocks.

29. The method of claim 27 wherein each successively added layer of medium has an electroendosmotic potential no less than the electroendosmotic potential of the immediately preceding layer of medium.

30. The method of claim 27 wherein each successively added layer of medium has an electroendosmotic potential no greater than the electroendosmotic potential of the immediately preceding layer of medium.

31. The method of claim 27 further comprising forming a plurality of ridges on the exposed surface of at least one of the added layers.

32. The method of claim 25 wherein said buffer block forming step further comprises filling cavities in a mold with media having a generally changing electroendosmotic potential.

33. The method of claim 32 further comprising the step of initially placing said substrate in said mold and thereafter casting said medium on top of said substrate to form a unitary electrophoresis plate having a continuum of electrophoretic media.

* * * * *